United States Patent [19]

Byrd, Jr. et al.

[11] Patent Number: 4,734,641
[45] Date of Patent: Mar. 29, 1988

[54] METHOD FOR THE THERMAL CHARACTERIZATION OF SEMICONDUCTOR PACKAGING SYSTEMS

[75] Inventors: Dee H. Byrd, Jr., Hillsboro; Michael H. Williams, Aloha, both of Oreg.

[73] Assignee: Tektronix, Inc., Beaverton, Oreg.

[21] Appl. No.: 23,595

[22] Filed: Mar. 9, 1987

[51] Int. Cl.⁴ ............................................. G01N 25/18
[52] U.S. Cl. ................................. 324/158 R; 374/44; 374/183
[58] Field of Search .................. 324/158 F, 158 R; 374/152, 1, 3, 44, 43, 183; 73/52

[56] References Cited

U.S. PATENT DOCUMENTS

| 4,186,368 | 1/1980 | White et al. | 338/28 |
| 4,684,884 | 8/1987 | Soderlund | 324/158 R X |
| 4,695,578 | 9/1987 | Manswia et al. | 324/158 R X |

FOREIGN PATENT DOCUMENTS 161649  12/1981  Japan ................................. 374/43

OTHER PUBLICATIONS

Rev. Sci. Instrum., Martin, et al., "Apparatus for Ice Point of Capsule Platinum Resistance Thermometers", vol. 45, No. 7, Jul. 1974, pp. 953–955.

*Electronics*, Bolvin, "Thermal Characteristics of ICs Gains in Importance", Oct. 31, 1974, pp. 87–90.

*Primary Examiner*—Reinhard J. Eisenzopf
*Assistant Examiner*—Stephen M. Baker
*Attorney, Agent, or Firm*—Jay K. Malkin; William S. Lovell

[57] ABSTRACT

A method for determining the thermal characteristics of a semiconductor packaging system is provided which uses a platinum resistor test unit. The platinum resistor is preferably sized to approximate the dimensions of the semiconductor device for which the package was designed, and is installed within the package. The packaged resistor is then thermally calibrated at a plurality of temperature levels to generate a linear temperature versus resistance graph or equation corresponding thereto. Next, voltage is applied to the packaged resistor causing such resistor to "self heat." Its resistance is calculated, and the temperature corresponding thereto is obtained from the graph or equation. Such temperature is the surface temperature of the resistor. This temperature may then be used to calculate the temperature gradient from the inside of the package to any reference point on or near the outside of the package, the temperature of which has been previously determined.

21 Claims, 4 Drawing Figures

METHOD FOR THE THERMAL CHARACTERIZATION OF SEMICONDUCTOR PACKAGING SYSTEMS

BACKGROUND OF THE INVENTION

The present invention generally relates to a method for the thermal characterization of packaging materials used to contain semiconductor devices, and more particularly to the use of a platinum resistor test unit designed to accomplish such characterization in a fast and efficient manner.

Semiconductor devices, including integrated circuits, are traditionally placed within packages designed to secure and contain the devices during operation. Typical packages include conventional DIP (dual-in-line) packages made of plastic, ceramic packages (CERDIP), hybrid units, metal can-type units, and flat pack small geometry units.

In determining the operational capabilities of a semiconductor device contained within a package, it is important to calculate the amount of heat the device will generate, and how effectively the heat is dissipated through the package. The life span of a semiconductor device is directly related to its operational temperature. It is therefore important to first determine the junction temperature ($T_j$) of the device during operation within its package. The "junction temperature" is defined as the temperature at the surface of the device while it is operating. Temperature extremes as small as 10° C. above the $T_j$ determined to be "critical" for a particular semiconductor device can reduce its operational lifetime by over one-half. Junction temperature values over 160° C. will almost always result in very early failure of the device.

Next, it is necessary in any semiconductor packaging system to determine the rate at which heat will flow from the semiconductor device out of its package. This heat flow is traditionally expressed in °C./watt. Having accurate information regarding the heat dissipation of a semiconductor device in its native environment (e.g. within its package) facilitates the manufacture of improved packaging systems and heat sink units associated therewith.

Traditionally, two methods have been used to thermally characterize semiconductors and their packaging systems. A general discussion of such methods may be found in the article "Semiconductor Thermal Considerations in System Design" by Siegel (December 1983, Sage Enterprises offprint article). The first of these methods involves the use of an infrared microscope system (IR method). The IR method uses an infrared detector coupled with an optical microscope. To characterize a semiconductor device within a package, the surface of the device must first be exposed. Using the optical microscope and attached infrared detector, the device can be scanned to generate an average temperature profile, or attention can be directed to individual points on the device.

However, there are certain disadvantages inherent in the IR method. First, the package containing the semiconductor device must be partially opened so that the surface of the device can be viewed. This prevents an accurate determination of the heat dissipation from the device in its native, packaged environment since a portion of the package and any heat sinks attached thereto must be removed.

In addition, the semiconductor device being tested must, in most cases, be coated with a special material having a constant emissivity. Such coating can alter the heat dissipation characteristics of the device, making accurate thermal analysis even more difficult. Other disadvantages of the IR method include high equipment and maintenance costs, and limited accuracy.

Another frequently used method is called the Pulsed Diode/Transistor $V_{be}$ method (PDT method). Most semiconductor devices have at least one temperature-dependent characteristic. In a transistor, the base to emitter voltage ($V_{be}$) is temperature-dependent. In a diode, the forward voltage ($V_f$) is temperature-dependent. The temperature-dependent characteristics of these devices may be plotted against externally-applied temperatures to yield a graph. The devices are then inserted within a selected package in place of the semiconductor for which it was designed, and a test simulation is run. By using data obtained from the simulation in conjunction with the previously-prepared graph, the thermal characteristics of the package can be determined under various operational conditions.

However, there are also numerous disadvantages inherent in the PDT method. First, it requires fairly expensive test equipment and is slow to use. In addition, it is not very accurate since the test device (transistor, diode, etc.) is a "point source" and does not consider the overall size of the semiconductor device for which the package was designed.

The present invention represents a substantial departure from the above-described methods in numerous aspects. Primarily, it avoids the use of expensive test equipment, while increasing the speed, accuracy, and ease with which the thermal characteristics of a semiconductor packaging system may be determined.

SUMMARY OF THE INVENTION

It is an object of the present invention to provide a method for determining the thermal characteristics of a semiconductor packaging system which avoids the use of expensive test equipment.

It is another object of the present invention to provide a method for determining the thermal characteristics of a semiconductor packaging system which involves a minimum number of operational procedures.

It is a further object of the present invention to provide a method for determining the thermal characteristics of a semiconductor packaging system which is capable of fast and accurate measurement under a wide range of operating conditions.

It is a still further object of the present invention to provide a method for determining the thermal characteristics of a semiconductor packaging system which can be used to analyze a semiconductor device in its native, packaged environment without physical destruction of the package.

It is an even further object of the present invention to provide a method for determining the thermal characteristics of a semiconductor packaging system which can take into consideration the size and dimensions of the semiconductor device for which the package was designed.

It is an even further object of the present invention to provide a method for determining the thermal characteristics of a semiconductor packaging system which is applicable to a wide variety of semiconductor devices, packaging materials, and heat sinking technologies.

To accomplish these objectives, a method for characterizing semiconductor packaging systems is provided which uses a platinum resistor test unit. The resistor includes a layer of platinum deposited on a substrate which is preferably sized to approximate the overall dimensions of the semiconductor device for which the packaging system was designed. Platinum is used because its resistance and temperature coefficient of resistance (TCR) are highly predictable and reproducible over a wide temperature range. The resistor is mounted and sealed within the selected package.

The resistance of the packaged resistor is then determined at multiple temperature levels in order to generate a mathematical correlation between temperature and resistance for the resistor. This mathematical correlation may take the form of either a temperature versus resistance graph, and/or a mathematical equation corresponding to the graph from which temperature values may be calculated at selected resistances.

Next, the packaged resistor is connected to a test circuit having a voltage source which causes the resistor to "self heat" because of the power it dissipates. Thereafter, the voltage across the resistor and current through the resistor is determined. Using this information, the resistance of the resistor can be calculated. The temperature at this resistance can then be obtained from the previously-prepared graph and/or mathematical equation. This temperature is the junction or surface temperature ($T_j$) of the resistor. Using the $T_j$ value thus obtained, the temperature gradient from the surface of the resistor to any pre-selected reference point on or near the outside of the package can be calculated.

The information obtained using the present invention is useful in determining the heat dissipation capabilities of the packaging system being tested, and represents an accurate simulation as to the amount of heat which will be dissipated through the package when the semiconductor device for which it was designed is installed. As a result, the packaging system can be designed to dissipate the maximum amount of heat.

These and other objects, features, and advantages of the invention will become apparent from the following detailed description of a preferred embodiment.

DETAILED DESCRIPTION OF A PREFERRED EMBODIMENT

The present invention represents a fast and efficient method for determining the thermal characteristics of a packaging system for a semiconductor device. Specifically, the invention enables an accurate determination to be made of the thermal gradient from the surface of a device within the package to any reference point on or near the outside of the package. Such information is useful for the reasons previously discussed.

Figure 1:
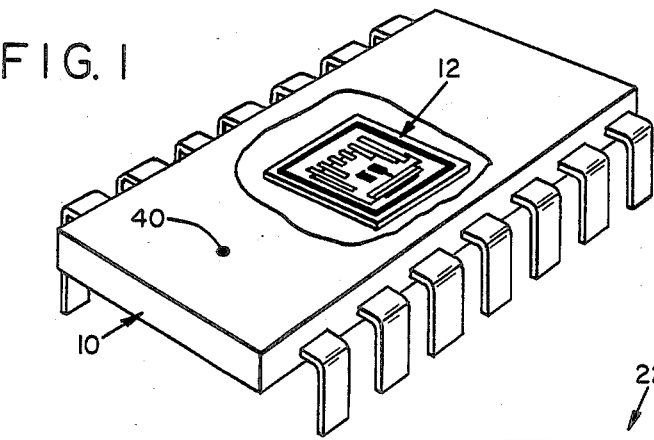
FIG. 1 is a perspective view of a DIP package having portions broken away to illustrate a platinum resistor constructed according to the present invention mounted therein.

To accomplish the method of the present invention, a semiconductor package is selected for which thermal characterization is desired. With reference to FIG. 1, a DIP (dual-in-line) package 10 is illustrated. In addition to this type of package, other packages may be characterized, including ceramic packages (CERDIP), hybrid units, flat pack small geometry packages, and metal can-type packages.

Figure 2:
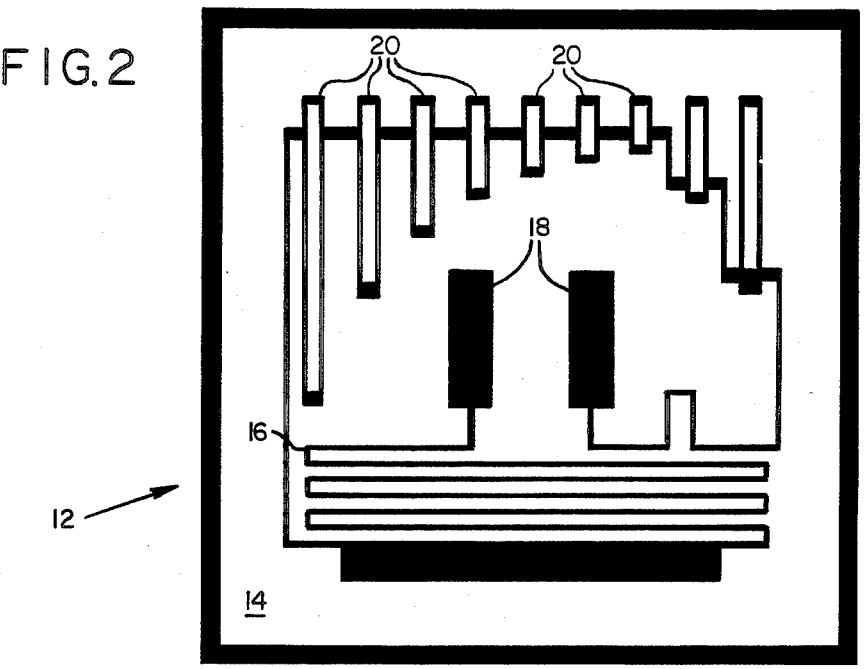
FIG. 2 is a top plan view of the platinum resistor of the present invention.

Sealed within the package 10 is a platinum resistor 12. The platinum resistor 12 is illustrated in FIG. 2, and comprises a substrate 14 (preferably silicon) having a platinum element 16 formed thereon in a serpentine pattern as shown in FIG. 2 to provide maximum resistance while using minimal surface area. The platinum element 16 is applied to the substrate 14 using conventional vacuum deposition or sputtering techniques at a thickness of approximately 7,000–10,000 Angstroms. Attached to the platinum element 16 are a plurality of gold terminal pads 18 to which external connection wires (not shown) are attached. A further discussion of the construction of the resistor 12 is set forth in U.S. Pat. No. 4,186,368 entitled "Wide Range, Quick Response Temperature Probe Sensor."

The pattern of the platinum element 16 is designed so that laser trimming or the like may be used to adjust its nominal resistance, if desired. For example, a plurality of trimmable elements 20 may be provided as shown in FIG. 2. Elements 20 comprise rectangular areas of platinum that may be selectively removed. It is preferred that a 100 ohm (0° C.) nominal resistance be used, although other values may be used ranging from 50 to 1,000 ohms, depending on the type of packaging system being tested, and the semiconductor device for which it was designed.

Platinum was selected for use in the resistor 12 because its resistance and temperature coefficient of resistance (TCR) are highly predictable and reproducible over a wide temperature range. For example, the resistance of a resistor constructed as described herein may be calculated according to the following second order polynomial equation:

$$R_t = R_s + [0.0037\ R_s * T] - [8.9 \times 10^{-7} R_s * T^2]$$

[$R_t$=Resistance in ohms at a selected temperature
T=selected temperature in °C.
$R_s$=nominal resistance at 0° C.]

The nominal resistance is a function of the thickness and length of the platinum resistor material, and is traditionally specified at 0° C. The 0.0037 and $8.9 \times 10_{-7}$ values in the equation represent the TCR of platinum.

In addition, the resistor 12 can be sized to approximate the overall dimensions of the semiconductor device for which the package 10 was designed. This enables a more accurate temperature profile to be obtained in comparison with other methods which make measurements only at single points.

Once the resistor 12 is mounted within the package 10, it is thermally calibrated. Thermal calibration involves subjecting the packaged resistor 12 to a first temperature ($T_1$) and measuring the resistance at such temperature. The resistance may be measured by using an ohm meter or other conventional test equipment known to those skilled in the art.

Next, the packaged resistor 12 is subjected to a second temperature ($T_2$) and the resistance thereof is measured in a similar manner. If desired, measurements at additional temperature levels ($T_3$, $T_4$ . . . ) can be taken.

Figure 3:
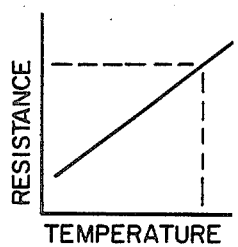
FIG. 3 is a representation of the temperature versus resistance graph which may be generated using the platinum register of the present invention.

A mathematical correlation between temperature and resistance relative to resistor 12 can now be prepared. For example, a graph of temperature versus resistance can be generated as illustrated in FIG. 3. Because of the above-described characteristics of platinum, the relationship between temperature and resistance is substantially linear as shown. In the alternative, once the resistances are obtained at the specified temperature levels, conventional regression analysis may be used to generate a mathematical equation corresponding to the graph of FIG. 3. The usefulness of this graph and/or mathematical equation will be more fully described below.

Thermal calibration of the packaged resistor 12 may be accomplished in numerous ways. For example, the packaged resistor 12 can first be immersed in an ice bath ($T_1 = 0°$ C.) and then subsequently immersed in boiling water ($T_2 = 100°$ C.). However, any procedure may be used which will involve exposure of the resistor 12 to at least two constant and readily determinable temperature values.

Figure 4:
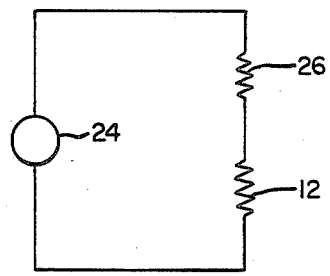
FIG. 4 is a schematic illustration of a test voltage circuit usable in the present invention as described herein.

The packaged resistor 12 can now be thermally characterized easily and accurately. First, the resistor 12 is connected to a test circuit having a voltage source. The applied voltage across the resistor 12 causes it to "self heat." This may be accomplished using a conventional voltage divider circuit 22 shown in FIG. 4 having a power supply 24 and fixed value resistor 26. A voltage divider circuit, as used herein, consists of a network of impedance elements connected in series from which one or more voltages can be obtained across any portion of the network. As shown in FIG. 4, resistor 12 is placed in series with fixed value resistor 26.

Next, the voltage ($V_1$) is measured across the resistor 26 and the voltage ($V_2$) is measured across resistor 12. The current in the circuit may then be calculated using the following expression derived from Ohm's law:

$$T = V_1/R \text{ fixed value resistor}$$

The resistance of the resistor 12 at the voltage delivered by the power supply 24 can now be calculated as follows:

$$R_{platinum} = V_2/I$$

The temperature corresponding to the $R_{platinum}$ value determined from the above expression can be obtained from the graph of FIG. 3 or the mathematical equation corresponding thereto. This temperature represents the surface or junction temperature ($T_j$) of the resistor 12.

Next, a reference position on the outside of the package 10 is selected. For example, a suitable reference position is illustrated in FIG. 1 at 40. The temperature at this reference position ($T_c$) during operation of the resistor is measured. Measurement may be accomplished using a thermocouple or other conventional temperature measurement device. In addition to reference positions on the surface of the package 10, reference positions may be selected at a predetermined distance away from the package 10. The term "on the outside" of the package 10 as used herein shall be construed to include all exterior reference positions on or away from the package 10.

Now, the temperature gradient ($T_{jc}$) from the surface of the resistor 12 to the selected reference position 40 can be calculated using the following equation:

$$T_{jc} = \frac{T_j - T_c}{V_2 * I}$$

$T_j$ = junction temperature of resistor 12
$T_c$ = temperature at the selected reference position
$V_2$ = voltage across resistor 12
$I$ = current in the circuit
$T_{jc}$ = temperature gradient from the surface of resistor 12 to the selected reference position in °C./watt Since resistor 12 can be prepared to approximate the size of the semiconductor device for which the package 10 was designed, the information thus obtained is valuable in illustrating how the system will operate and dissipate heat under actual service conditions. The package 10 can then be appropriately modified and/or heat sink devices may be secured thereto if necessary.

EXAMPLE

The following example will illustrate the ability of the present invention to thermally characterize a semiconductor package. First, a resistor 12 having a nominal resistance of 100 ohms at 0° C. was inserted into a package 10, and subsequently calibrated to generate a temperature versus resistance graph similar to that shown in FIG. 3. Calibration occurred at 0° C. ($T_1$) and 100° C. ($T_2$) using ice and boiling water baths, respectively. The resistance of the resistor 12 at 0° C. was 100.2 ohms and the resistance of the resistor 12 at 100° C. was 138 ohms.

To apply voltage to the resistor 12, the voltage divider circuit of FIG. 4 was used. The circuit included a 10 volt power supply 24 and 100 ohm fixed resistor 26.

The voltage across resistor 26 was measured and determined to be 4 volts ($V_1$). The voltage across resistor 12 was also measured and determined to be 6 volts ($V_2$). The current in the circuit was then calculated as follows:

$$I = V_1/R_{fixed} = 4V/100 \text{ ohms} = 40 \text{ mA}$$

Next, the resistance of resistor 12 was calculated as follows:

$$R_{platinum} = V_2/I = 6V/40mA = 150 \text{ ohms}$$

The resistance value of resistor 12 increased from 100 ohms to 150 ohms due to the power being dissipated in the resistor as it generated heat.

The temperature of resistor 12 at 150 ohms was then determined to be approximately 135° C. using the previously-generated temperature versus resistance graph. In the alternative, such temperature could have been calculated using the following series of equations corresponding to the aforesaid graph:

$$m = \frac{(y_2 - y_1)}{(x_2 - x_1)}$$

[m = slope
$y_2$ = resistance at $T_2$
$Y_1$ = resistance at $T_1$
$x_2 = T_2$
$x_1 = T_1$]

$$m = \frac{(138 \text{ ohms} - 100.2 \text{ ohms})}{(100° \text{ C.} - 0° \text{ C.})}$$

-continued
$$m = \frac{37.8 \text{ ohms}}{100° \text{ C.}} = 0.378$$

Using this information, the following calculations can be made:

$$m = \frac{z_2 - x_2}{z_1 - x_1}$$

[m=slope=0.378
$z_2$=resistance of resistor 12 during during operation of test circuit (150 ohms)
$x_2$=resistance at $T_2$
$z_1$=temperature of resistor at 150 ohms
$x_1$=$T_2$]

$$0.378 = \frac{150 \text{ ohms} - 138 \text{ ohms}}{z_1 - 100° \text{ C.}}$$

$$0.378 = \frac{12 \text{ ohms}}{z_1 - 100° \text{ C.}}$$

$$0.378 * z_1 - 37.8 = 12$$

$$0.378 * z_1 = 49.8$$

$$z_1 = 135° \text{ C. (approximate)}$$

Next, a reference position on the outside of the package 10 was selected corresponding to that shown at 40 in FIG. 1. The temperature at this position was determined to be 90° C.

Using the aforesaid data, $T_{jc}$ for the packaged resistor 12 was then calculated as follows:

$$T_{jc} = \frac{T_j - T_c}{V_2 * I} = \frac{135° \text{ C.} - 90° \text{ C.}}{6V \times 40 \text{ mA}} = 187.5° \text{ C./watt}$$

Having herein described a preferred embodiment of the present invention, it will be appreciated by those of ordinary skill in the art that suitable changes and modifications may be made within the scope of the present invention. For example, the size, dimensions, and other physical characteristics of the materials disclosed herein may be varied. In addition, assembly and test instruments used in association with the present invention may be changed, including the means used to initially apply voltage to the resistor of the invention. Thus, the scope of the present invention shall be defined in accordance with the following claims.

What is claimed is:

1. A method for measuring the thermal characteristics of a packaging system for semiconductors comprising:
    providing a resistor comprising a substrate having a layer of platinum deposited thereon;
    mounting said resistor within a package designed for the containment of a semiconductor device;
    thermally calibrating said resistor within said package to obtain a mathematical correlation between temperature and resistance for said resistor;
    connecting said resistor to a test circuit having a voltage source therein;
    determining the voltage across said resistor and the resistance thereof during the operation of said circuit;
    using said mathematical correlation to obtain a temperature value corresponding to said resistance of said resistor during the operation of said circuit, said temperature value representing the temperature at the surface of said resistor during its operation;
    selecting a reference point on the outside of said package;
    measuring the temperature at said reference point during the operation of said circuit; and
    calculating the temperature gradient between the surface of said resistor and said reference point.

2. The method of claim 1 wherein said thermal calibration of said resistor comprises:
    subjecting said resistor within said package to at least two different temperatures;
    determining the resistance of said resistor at each of said temperatures; and
    generating a mathematical correlation between temperature and resistance for said resistor using said temperatures and resistances corresponding thereto.

3. The method of claim 2 wherein said mathematical correlation comprises a linear temperature versus resistance graph which may be used to obtain temperature values corresponding to any selected resistance values.

4. The method of claim 2 wherein said mathematical correlation comprises an equation which may be used to obtain temperature values corresponding to any selected resistance values.

5. The method of claim 1 wherein said resistance of said resistor is determined by measuring the current through said resistor, and dividing said voltage across said resistor by said current.

6. The method of claim 5 wherein said temperature gradient is calculated according to the expression:

$$T_{jc} = \frac{T_j - T_c}{V * I}$$

wherein
    $T_j$=the temperature at the surface of said resistor
    $T_c$=the temperature at said reference point
    I=the current through said resistor
    V=the voltage across said resistor
    $T_{jc}$=the temperature gradient in ° C./watt between said surface of said resistor and said reference point.

7. The method of claim 1 wherein said resistor is sized to approximate the dimensions of the semiconductor device for which said package was designed.

8. The method of claim 1 wherein said resistor comprises a silicon substrate.

9. The method of claim 1 wherein said layer of platinum is deposited on said substrate at a thickness of about 7,000 to 10,000 Angstroms.

10. The method of claim 1 wherein said resistor comprises a plurality of gold terminal pads attached thereto.

11. A method for measuring the thermal characteristics of a packaging system for semiconductors comprising:
    providing a resistor comprising a substrate having a layer of platinum deposited thereon;
    mounting said resistor within a package designed for the containment of a semiconductor device;
    thermally calibrating said resistor within said package by subjecting said resistor within said package to at least two different temperatures, determining the resistance of said resistor at each of said temperatures, and generating a mathematical correlation between temperature and resistance for said resistor using said temperatures and resistances corresponding thereto;

connecting said resistor to a test circuit having a voltage source therein;

determining the voltage across said resistor;

determining the resistance of said resistor during the operation of said circuit by measuring the current through said resistor, and dividing said voltage across said resistor by said current;

using said mathematical correlation to obtain a temperature value corresponding to said resistance of said resistor during the operation of said circuit, said temperature value representing the temperature at the surface of said resistor during its operation;

selecting a reference point on the outside of said package;

measuring the temperature at said reference point during the operation of said circuit; and calculating the temperature gradient between the surface of said resistor and said reference point.

12. The method of claim 11 wherein said resistor is sized to approximate the dimensions of the semiconductor device for which said package was designed.

13. The method of claim 11 wherein said resistor comprises a silicon substrate.

14. The method of claim 11 wherein said layer of platinum is deposited on said substrate at a thickness of about 7,000 to 10,000 Angstroms.

15. The method of claim 11 wherein said resistor comprises a plurality of gold terminal pads attached thereto.

16. The method of claim 11 wherein said temperature gradient is calculated according to the expression:

$$T_{jc} = \frac{T_j - T_c}{V * I}$$

wherein $T_j$ = the temperature at the surface of said resistor
$T_c$ = the temperature at said reference point
$I$ = the current through said resistor
$V$ = the voltage across said resistor
$T_{jc}$ = the temperature gradient in °C./watt between said surface of said resistor and said reference point.

17. The method of claim 11 wherein said mathematical correlation comprises a linear temperature versus resistance graph which may be used to obtain temperature values corresponding to any selected resistance values.

18. The method of claim 11 wherein said mathematical correlation comprises an equation which may be used to obtain temperature values corresponding to any selected resistance values.

19. A method for measuring the thermal characteristics of a packaging system for semiconductors comprising:

providing a package designed for the containment of a semiconductor device;

providing a resistor sized to approximate the dimensions of the semiconductor device for which said package was designed, said resistor comprising a silicon substrate having a layer of platinum deposited thereon at a thickness of about 7,000 to 10,000 Angstroms;

mounting said resistor within said package;

thermally calibrating said resistor within said package by subjecting said resistor within said package to at least two different temperatures, determining the resistance of said resistor at each of said temperatures, and generating a mathematical correlation between temperature and resistance for said resistor using said temperatures and resistances corresponding thereto;

connecting said resistor to a test circuit having a voltage source therein;

determining the voltage across said resistor;

determining the resistance of said resistor during the operation of said circuit by measuring the current through said resistor, and dividing said voltage across said resistor by said current;

using said mathematical correlation to obtain a temperature value corresponding to said resistance of said resistor during the operation of said circuit, said temperature value representing the temperature at the surface of said resistor during its operation;

selecting a reference point on the outside of said package;

measuring the temperature at said reference point during the operation of said circuit; and calculating the temperature gradient between the surface of said resistor and said reference point, said gradient being calculated according to the expression:

$$T_{jc} = \frac{T_j - T_c}{V * I}$$

wherein $I_j$ = the temperature at the surface of said resistor
$T_c$ = the temperature at said reference point
$I$ = the current through said resistor
$V$ = the voltage across said resistor
$T_{jc}$ = the temperature gradient in °C./watt between said surrace of said resistor and said reference point 20. The method of claim 19 wherein said mathematical correlation comprises a linear temperature versus resistance graph which may be used to obtain temperature values corresponding to any selected resistance values.

21. The method of claim 19 wherein said mathematical correlation comprises an equation which may be used to obtain temperature values corresponding to any selected resistance values.

* * * * *